US009879002B2

(12) United States Patent
Gage et al.

(10) Patent No.: US 9,879,002 B2
(45) Date of Patent: Jan. 30, 2018

(54) PDE10 INHIBITORS AND RELATED COMPOSITIONS AND METHODS

(71) Applicant: Omeros Corporation, Seattle, WA (US)

(72) Inventors: Jennifer Lynn Gage, Kenmore, WA (US); Kevin L. Harbol, Bothell, WA (US); Raghuram Bommagani, Hyderabad (IN); Durga Varaprasad Botla, Hyderabad (IN); Laxma Reddy Karnati, Secunderabad (IN); Satyamurthi Narayanan, Secunderabad (IN)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 15/136,699

(22) Filed: Apr. 22, 2016

(65) Prior Publication Data
US 2017/0022190 A1    Jan. 26, 2017

Related U.S. Application Data

(60) Provisional application No. 62/152,736, filed on Apr. 24, 2015.

(51) Int. Cl.
*C07D 417/10* (2006.01)
*C07H 15/26* (2006.01)

(52) U.S. Cl.
CPC .......... *C07D 417/10* (2013.01); *C07H 15/26* (2013.01)

(58) Field of Classification Search
None
See application file for complete search history.

(56) References Cited

U.S. PATENT DOCUMENTS

| 5,693,652 | A | 12/1997 | Takase et al. | |
|---|---|---|---|---|
| 6,177,154 | B1 | 1/2001 | Matsui et al. | |
| 6,197,901 | B1 | 3/2001 | Rohde et al. | |
| 6,403,805 | B1 | 6/2002 | Freyne et al. | |
| 7,053,192 | B2 | 5/2006 | Li et al. | |
| 7,129,238 | B2 | 10/2006 | Banner et al. | |
| 7,449,486 | B2 | 11/2008 | Hans et al. | |
| 7,786,139 | B2 | 8/2010 | Bergmann et al. | |
| 8,278,327 | B2 | 10/2012 | Bergmann et al. | |
| 8,343,970 | B2 * | 1/2013 | Cutshall | C07D 231/12 514/231.5 |
| 8,377,930 | B2 | 2/2013 | Cutshall et al. | |
| 8,685,975 | B2 * | 4/2014 | Cutshall | C07D 231/12 514/231.5 |
| 9,102,643 | B2 * | 8/2015 | Cutshall | C07D 231/12 |
| 9,434,707 | B2 * | 9/2016 | Cutshall | C07D 231/12 |
| 2003/0032579 | A1 | 2/2003 | Lebel et al. | |
| 2005/0135999 | A1 | 6/2005 | Elomari et al. | |
| 2006/0074102 | A1 | 4/2006 | Cusack et al. | |
| 2006/0128695 | A1 | 6/2006 | Bourguignon et al. | |
| 2007/0032435 | A1 | 2/2007 | Alani et al. | |
| 2007/0032531 | A1 | 2/2007 | Smith et al. | |
| 2007/0249544 | A1 | 10/2007 | Himmelsbach et al. | |
| 2008/0004448 | A1 | 1/2008 | Wayne et al. | |
| 2008/0089835 | A1 | 4/2008 | Burton | |
| 2008/0090834 | A1 | 4/2008 | Hoover et al. | |
| 2008/0103186 | A1 | 5/2008 | Glover et al. | |
| 2008/0139569 | A1 | 6/2008 | Rocco et al. | |
| 2008/0319024 | A1 | 12/2008 | Greil et al. | |
| 2009/0069281 | A1 | 3/2009 | Austad et al. | |
| 2009/0124652 | A1 | 5/2009 | Ach et al. | |
| 2009/0137794 | A1 | 5/2009 | Mendez et al. | |
| 2009/0176829 | A1 | 7/2009 | Verhoest et al. | |
| 2009/0176983 | A1 | 7/2009 | Dova et al. | |
| 2009/0203705 | A1 | 8/2009 | Biagetti et al. | |
| 2009/0221586 | A1 | 9/2009 | Okada et al. | |
| 2009/0239946 | A1 | 9/2009 | McKeown et al. | |
| 2010/0021539 | A1 | 1/2010 | Kowalski et al. | |
| 2010/0035872 | A1 | 2/2010 | Cutshall et al. | |

(Continued)

FOREIGN PATENT DOCUMENTS

DE    43 23 192 A1    1/1995
DE    43 25 846 C1    1/1995

(Continued)

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Aggarwal et al., "A Novel One-Pot Method for the Preparation of Pyrazoles by 1,3-Dipolar Cycloadditions of Diazo Compounds Generated in Situ," *J. Org. Chem.* 68(13):5381-5383, 2003.
Background Information for the ACPS Meeting, "Scientific Considerations of Polymorphism in Pharmaceutical Solids: Abbreviated New Drug Applications," *ACPS Meeting* Oct. 2002, http://www.fda.gov/ohrms/dockets/ac/02/briefing/3900B1_04_polymorphism.htm, Jan. 25, 2006, 5 pages.
Dias et al., "Synthesis and analgesic properties of 5-acyl-arylhydrazone 1-H pyrazolo [3,4-b] pyridine derivatives," *Pharmaceutica Acta Helvetiae* 69:163-196, 1994.

(Continued)

*Primary Examiner* — Traviss C McIntosh, III
(74) *Attorney, Agent, or Firm* — Seed IP Law Group LLP

(57) ABSTRACT

Isolated or pure compounds that inhibit PDE10 are disclosed that have utility in the treatment of a variety of conditions, including but not limited to psychotic, anxiety, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, drug-induced psychosis and panic and obsessive-compulsive disorders. Pharmaceutically acceptable salts, stereoisomers, solvates and prodrugs of the compounds are also provided. Also disclosed are compositions containing an isolated or pure compound in combination with a pharmaceutically acceptable carrier, as well as methods relating to the use thereof for inhibiting PDE10 in a warm-blooded animal in need of the same.

29 Claims, No Drawings

(56) References Cited

U.S. PATENT DOCUMENTS

| | | | |
|---|---|---|---|
| 2010/0035887 | A1 | 2/2010 | Ricciardi |
| 2013/0158081 | A1 | 6/2013 | Almstead et al. |
| 2013/0196994 | A1 | 8/2013 | Cutshall et al. |
| 2014/0228581 | A1 | 8/2014 | Cutshall et al. |

FOREIGN PATENT DOCUMENTS

| | | | |
|---|---|---|---|
| DE | 43 43 286 A1 | 6/1995 | |
| EP | 0 672 880 A1 | 9/1995 | |
| EP | 1 568 691 A1 | 8/2005 | |
| WO | 92/01679 A1 | 2/1992 | |
| WO | 94/12461 A1 | 6/1994 | |
| WO | 96/00218 A1 | 1/1996 | |
| WO | 96/15096 A1 | 5/1996 | |
| WO | 96/31485 A1 | 10/1996 | |
| WO | 96/31486 A1 | 10/1996 | |
| WO | 96/41609 A2 | 12/1996 | |
| WO | 97/27190 A1 | 7/1997 | |
| WO | 98/08830 A1 | 3/1998 | |
| WO | 99/45914 A1 | 9/1999 | |
| WO | 00/34254 A1 | 6/2000 | |
| WO | 00/55139 A2 | 9/2000 | |
| WO | 01/41807 A2 | 6/2001 | |
| WO | 01/44226 A1 | 6/2001 | |
| WO | 01/96334 A2 | 12/2001 | |
| WO | 2004/011410 A1 | 2/2004 | |
| WO | 2004/033652 A2 | 4/2004 | |
| WO | 2004/058254 A1 | 7/2004 | |
| WO | 2004/071509 A1 | 8/2004 | |
| WO | 2004/094411 A1 | 11/2004 | |
| WO | 2005/103022 A1 | 11/2005 | |
| WO | 2006/072828 A2 | 7/2006 | |
| WO | 2006/084186 A2 | 8/2006 | |
| WO | 2006/116355 A1 | 11/2006 | |
| WO | 2007/058338 A2 | 5/2007 | |
| WO | 2007/073299 A1 | 6/2007 | |
| WO | 2008/031014 A1 | 3/2008 | |
| WO | 2008/040669 A2 | 4/2008 | |
| WO | 2008/064342 A2 | 5/2008 | |
| WO | 2009/010156 A2 | 1/2009 | |
| WO | 2009/049022 A1 | 4/2009 | |
| WO | 2009/143178 A2 | 11/2009 | |
| WO | 2009/152825 A1 | 12/2009 | |
| WO | 2010/017236 A1 | 2/2010 | |
| WO | 2011/112828 A1 | 9/2011 | |

OTHER PUBLICATIONS

Enders et al., "N-heterocyclic carbene catalysed asymmetric cross-benzoin reactions of heteroaromatic aldehydes with trifluoromethyl ketones," *Chem. Commun.* 46(34):6282-6284, 2010.
Fraga et al., "Synthesis and pharmacological evaluation of novel heterotricyclic acylhydrazone derivatives, designed as PAF antagonists," *European Journal of Pharmaceutical Sciences* 11:285-290, 2000.
Fujishige et al., "Cloning and Characterization of a Novel Human Phosphodiesterase That Hydrolyzes Both cAMP and cGMP (PDE10A)," *The Journal of Biological Chemistry* 274(26):18438-18445, 1999.
Good et al., "The Synthesis of Oxazolo[3,2-a]pyridinium Salts," *J. Chem. Soc.* 14:1938-45, 1970.
Hashmi et al., "Bisphenols from Furfurals by Organocatalysis and Gold Catalysis," *SYNLETT* 11:1747-1752, 2007.
Hashmi et al., "Gold Catalysis: Desymmetrization in the Furan—Yne Reaction," *Synthesis* 13:2297-2307, 2010.
Kamitori et al., "Convenient Synthesis of 5-Trifluoromethyl-3-Oxazolines and 5-Trifluoromethyloxazoles," *Heterocycles* 34(5):1047-1054, 1992.
Lee et al., "Discotic liquid crystalline materials for potential non-linear optical applications: synthesis and liquid crystalline behavior of 1,3,5-triphenyl-2,4,6-triazine derivatives containing achiral and chiral alkyl chains at the periphery," *Tetrahedron Letters* 45:1019-1022, 2004.
Loughney et al., "Isolation and characterization of PDE10A, a novel human 3', 5'-cyclic nucleotide phosphodiesterase," *Gene* 234:109-117, 1999.
Lugnier, C., "Cyclic nucleotide phosphodiesterase (PDE) superfamily: A new target for the development of specific therapeutic agents," *Pharmacology & Therapeutics* 109(3):366-398, 2006.
Olin et al., "Synthesis of 4-Phenylthiazole-2-Methanol and Some of Its Derivatives. VIII," *J[Am] Chem Soc* 53:1470-1473, Apr. 6, 1931.
Okamoto et al., "Chiral HPLC for efficient resolution of enantiomers," *Chem. Soc. Rev.* 37:2593-2608, 2008.
Pirrung et al., "Multicomponent Reactions of Convertible Isonitriles," *J. Org. Chem.* 74(11):4110-4117, 2009.
Rodriguez-Spong et al., "General principles of pharmaceutical solid polymorphism: a supramolecular perspective," *Advanced Drug Delivery Reviews* 56:241-274, 2004.
PUBCHEM, Substance Record for SID 125300724, Nov. 10, 2011, https://pubchem.ncbi.nlm.nih.gov/substance/125300724, Aug. 10, 2016, 5 pages.
Soderling et al., "Isolation and characterization of a dual-substrate phosphodiesterase gene family: PDE10A," *Proc. Natl. Acad. Sci. USA* 96:7071-7076, Jun. 1999.
Soderling et al., "Regulation of cAMP and cGMP signaling: new phosphodiesterases and new functions," *Current Opinion in Cell biology* 12:174-179, 2000.
Tanaka et al., "Inhibitors of Acyl-CoA:Cholesterol O-Acyltransferase. 2. Identification and Structure-Activity Relationships of a Novel Series of N-Alkyl-N-(heteroaryl-substituted benzyl)-N-arylureas," *J. Med. Chem.* 41(13):2390-2410, 1998.
Thompson et al., "Multiple Cyclic Nucleotide Phosphodiesterase Activities from Rat Brain," *Biochemistry* 10(2):311-316, 1971.
Wilson et al., "Emerging Biology of PDE10A," *Current Pharmaceutical Design* 21:1-11, 2015.
Zafrani et al, "Diethyl bromodifluoromethylphosphonate: a highly efficient and environmentally benign difluorocarbene precursor," *Tetrahedron* 65:5278-5283, 2009.
PCT International Search Report for International Application No. PCT/US11/27927, dated Apr. 29, 2011, 3 pages.
PCT Written Opinion of the International Searching Authority for International Application No. PCT/US2011/027927, dated Apr. 29, 2011, 6 pages.
International Preliminary Report on Patentability for PCT International Application No. PCT/US2011/027927, dated Sep. 18, 2012, 7 pages.
International Search Report and Written Opinion dated Jul. 21, 2015, for International Application No. PCT/US2015/027645, 17 pages.
International Search Report and Written Opinion dated Jul. 13, 2015, for International Application No. PCT/US2015/027647, 17 pages.
International Search Report and Written Opinion dated Sep. 14, 2016, for International Application No. PCT/US2016/028973, 12 pages.

\* cited by examiner

PDE10 INHIBITORS AND RELATED COMPOSITIONS AND METHODS

CROSS-REFERENCE TO RELATED APPLICATIONS

This application claims the benefit under 35 U.S.C. §119 (e) of U.S. Provisional Patent Application No. 62/152,736, filed Apr. 24, 2015, which application is incorporated herein by reference in its entirety.

BACKGROUND

Technical Field

This invention relates generally to compounds having activity as PDE10 inhibitors, and to compositions containing the same, as well as to methods of treating various disorders by administration of such compounds to a warm-blooded animal in need thereof.

Description of the Related Art

Cyclic nucleotide phosphodiesterases (PDEs) are represented by a large superfamily of enzymes. PDEs are known to possess a modular architecture, with a conserved catalytic domain proximal to the carboxyl terminus, and regulatory domains or motifs often near the amino terminus. The PDE superfamily currently includes more than twenty different genes subgrouped into eleven PDE families (Lugnier, C., "Cyclic nucleotide phosphodiesterase (PDE) superfamily: a new target for the development of specific therapeutic agents." *Pharmacol Ther.* 2006 March; 109(3):366-98).

A recently described PDE, PDE10, was reported simultaneously by three independent groups (Fujishige et al., "Cloning and characterization of a novel human phosphodiesterase that hydrolyzes both cAMP and cGMP (PDE10A)," *J Biol Chem* 1999, 274:18438-18445; Loughney et al., "Isolation and characterization of PDE10A, a novel human 3', 5'-cyclic nucleotide phosphodiesterase," *Gene* 1999, 234: 109-117; Soderling et al., "Isolation and characterization of a dual-substrate phosphodiesterase gene family: PDE10A," *Proc Natl Acad Sci USA* 1999, 96:7071-7076). PDE10 has the capacity to hydrolyze both cAMP and cGMP; however, the $K_m$ for cAMP is approximately 0.05 μM, whereas the $K_M$ for cGMP is 3 μM. In addition, the $V_{max}$ for cAMP hydrolysis is fivefold lower than for cGMP. Because of these kinetics, cGMP hydrolysis by PDE10 is potently inhibited by cAMP in vitro, suggesting that PDE10 may function as a cAMP-inhibited cGMP phosphodiesterase in vivo. Unlike PDE8 or PDE9, PDE10 is inhibited by IBMX with an $IC_{50}$ (50% inhibitory concentration) of 2.6 μM. (See Soderling and Beavo, "Regulation of cAMP and cGMP signaling: new phosphodiesterases and new functions," *Current Opinion in Cell Biology,* 2000, 12:174-179.)

PDE10 contains two amino-terminal domains that are similar to the cGMP-binding domains of PDE2, PDE5 and PDE6, which are domains conserved across a wide variety of proteins. Because of the wide conservation of this domain, it is now referred to as the GAF domain (for the GAF proteins: cGMP binding phosphodiesterases; the cyanobacterial *Anabaena* adenylyl cyclase; and the *Escherichia coli* transcriptional regulator fh1A). Although in PDE2, PDE5 and PDE6 the GAF domains bind cGMP, this is probably not the primary function of this domain in all cases (e.g., *E. coli* are not thought to synthesize cGMP). Interestingly, in vitro binding studies of PDE10 indicate the dissociation constant ($K_d$) for cGMP binding is well above 9 μM. As in vivo concentrations of cGMP are not thought to reach such high levels in most cells, it seems likely that either the affinity of PDE10 for cGMP is increased by regulation, or that the primary function of the GAF domain in PDE10 may be for something other than cGMP binding.

Inhibitors of the PDE family of enzymes have widely been sought for a broad indication of therapeutic uses. Reported therapeutic uses of PDE inhibitors include allergies, obtrusive lung disease, hypertension, renal carcinoma, angina, congestive heart failure, depression and erectile dysfunction (WO 01/41807 A2). Other inhibitors of PDE have been disclosed for treatment of ischemic heart conditions (U.S. Pat. No. 5,693,652). More specifically, inhibitors of PDE10 have been disclosed for treatment of certain neurological and psychiatric disorders including, Parkinson's disease, Huntington's disease, schizophrenia, delusional disorders, drug-induced psychosis and panic and obsessive-compulsive disorders (Patent Publication No. U.S. 2003/0032579). PDE10 has been shown to be present at high levels in neurons in areas of the brain that are closely associated with many neurological and psychiatric disorders. By inhibiting PDE10 activity, levels of cAMP and cGMP are increased within neurons, and the ability of these neurons to function properly is thereby improved. Thus, inhibition of PDE10 is believed to be useful in the treatment of a wide variety of conditions or disorders that would benefit from increasing levels of cAMP and cGMP within neurons, including those neurological, psychotic, anxiety and/or movement disorders mentioned above.

Advances have been made with regard to inhibition of PDE10 as disclosed in U.S. Pat. Nos. 8,343,970 and 8,685,975, which are incorporated by reference in their entirety for all purposes. While such compounds have favorable therapeutic characteristics, there remains a need in the field for inhibitors of PDE10 with improved properties, e.g., solubility, while retaining effective levels of activity for the treatment of various conditions and/or disorders that would benefit from the same. The compounds of the present invention provide improved aqueous solubility compared to those of U.S. Pat. Nos. 8,343,970 and 8,685,975, while providing similar levels of therapeutic activity.

BRIEF SUMMARY

This invention is generally directed to isolated or substantially pure compounds that have activity as PDE10 inhibitors, as well as to methods for their preparation and use, and to pharmaceutical compositions containing the same.

In one embodiment, the compounds have the following general structure (I):

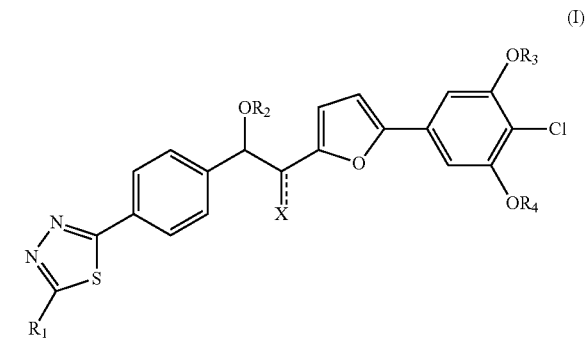

(I)

including pharmaceutically acceptable salts, stereoisomers, solvates and prodrugs thereof, wherein X, $R_1$, $R_2$, $R_3$, and $R_4$ are as defined below.

The compounds of this invention have utility over a wide range of therapeutic applications, and may be used to treat a wide variety of conditions or disorders that would benefit from increasing levels of cAMP and cGMP, especially within neurons, including (but not limited to) neurological disorders, such as psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias, and multiple sclerosis.

The methods of this invention include administering an effective amount of a compound of the foregoing structures, typically in the form of a pharmaceutical composition, to a mammal in need thereof, including a human. Thus, in a further embodiment, pharmaceutical compositions are disclosed containing one or more compounds of the foregoing structures in combination with a pharmaceutically acceptable carrier or diluent.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION

The present invention is directed generally to isolated or substantially pure compounds useful as PDE10 inhibitors, as well as to methods for their preparation and use, and to pharmaceutical compositions comprising the same.

In one embodiment, the PDE10 inhibitors of the present invention have the following structure (I):

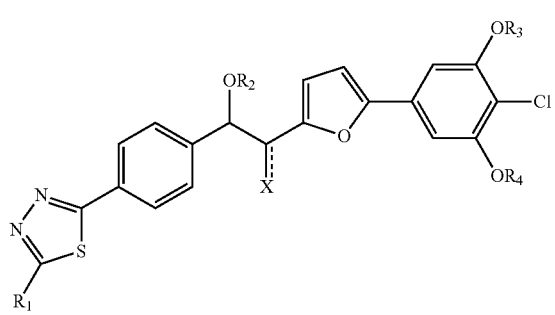

(I)

or a pharmaceutically acceptable salt, stereoisomer, solvate, or prodrug thereof, wherein:

$R_1$ is H, $C_{1-3}$ alkyl, hydroxy-$C_{1-3}$ alkyl, $C_1$-$C_3$ alkoxy, $C_{1-3}$ alkyl hydroxyl, or glucuronidyl-O—$C_{1-3}$ alkyl;

$R_2$ is H, $C_{1-3}$ alkyl, or glucuronidyl;

R3 and R4 are each independently H, $C_{1-3}$ alkyl, or glucuronidyl; and

X is =O, —OH, or —O-glucuronidyl, with the proviso that said compound of structure (I) is not:

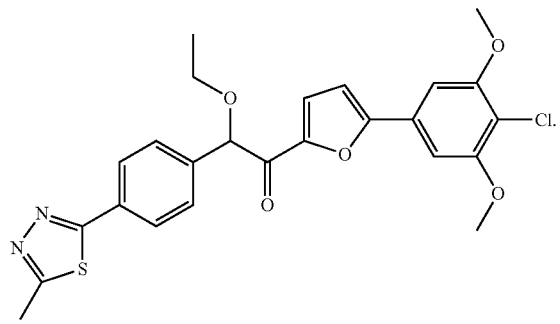 [SMILES: CCOC(C(=O)c1ccc(-c2cc(OC)c(Cl)c(OC)c2)o1)c1ccc(-c2nnc(C)s2)cc1]

As used herein, the above terms have the following meaning:

"Hydroxy" or "hydroxyl" refers to the —OH radical.

"Oxo" refers to the =O sub stituent.

"$C_{1-6}$alkyl" means a straight chain or branched, noncyclic or cyclic, unsaturated or saturated aliphatic hydrocarbon radical containing from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{1-6}$alkoxy" refers to a radical of the formula —$OR_a$ where $R_a$ is an alkyl radical as defined above, for example, methoxy, ethoxy, and the like.

"Halo" or "halogen" refers to bromo, chloro, fluoro, or iodo.

"Gluc" or "glucuronidyl" refers to glucuronide or glucuronoside group, such as β-D-glucuronide. That is any glucuronic acid group bound by a glycosidic bond, for example, a β-glycosidic bond. The "Gluc" group can be attached to a compound of structure (I) through any hydroxyl or carbonyl group.

The term "substituted" as used herein (for example, in the context of a substituted heterocyclyl or substituted aryl) means that at least one hydrogen atom is replaced with a substituent. "Substituents" within the context of this invention include halogen, hydroxy, oxo, cyano, nitro, imino, thioxo, amino, alkylamino, dialkylamino, alkyl, alkoxy, alkylthio, haloalkyl, aryl, aralkyl, heteroaryl, heteroarylalkyl, heterocycle and heterocyclealkyl, as well as —$NR_aR_b$, —$NR_aC(=O)R_b$, —$NR_aC(=O)NR_aNR_b$, —$NR_aC(=O)OR_b$, —$NR_aSO_2R_b$, —C(=O)$R_a$, —C(=O)$OR_a$, —C(=O)$NR_aR_b$, —OC(=O)$NR_aR_b$, —$OR_a$, —$SR_a$, —$SOR_a$, —S(=O)$_2R_a$, —OS(=O)$_2R_a$, —S(=O)$_2OR_a$, =$NSO_2R_a$ and —$SO_2NR_aR_b$. In the foregoing, $R_a$ and $R_b$ in this context may be the same or different and, independently, hydrogen, alkyl, haloalkyl, cycloalkyl, aryl, aralkyl, heterocyclyl. In addition, the foregoing substituents may be further substituted with one or more of the above substituents.

In other further embodiments of structure (I), $R_1$ is methyl or hydroxymethyl.

In other further embodiments of structure (I), $R_2$ is ethyl.

In other further embodiments of structure (I), $R_3$ and $R_4$ are each independently H, methyl, or glucuronidyl. In another embodiment of structure (I), $R_3$ and $R_4$ are each independently H or methyl.

In other further embodiments of structure (I), X is =O or —OH.

In other further embodiments of structure (I), the compound is selected from one of the following:

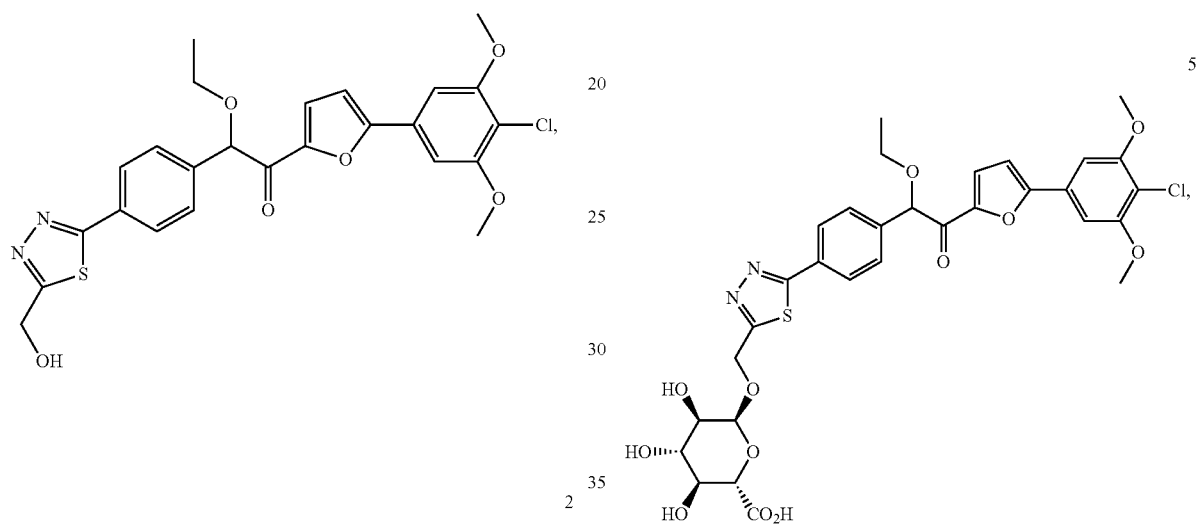

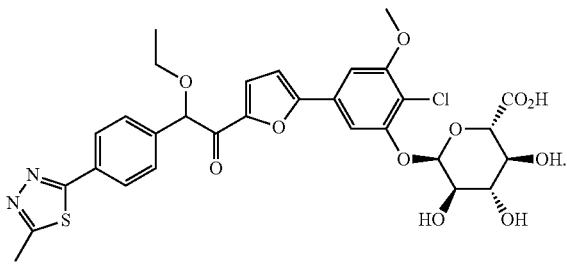

In one embodiment, the PDE10 inhibitor of the present invention is selected from one of the following:

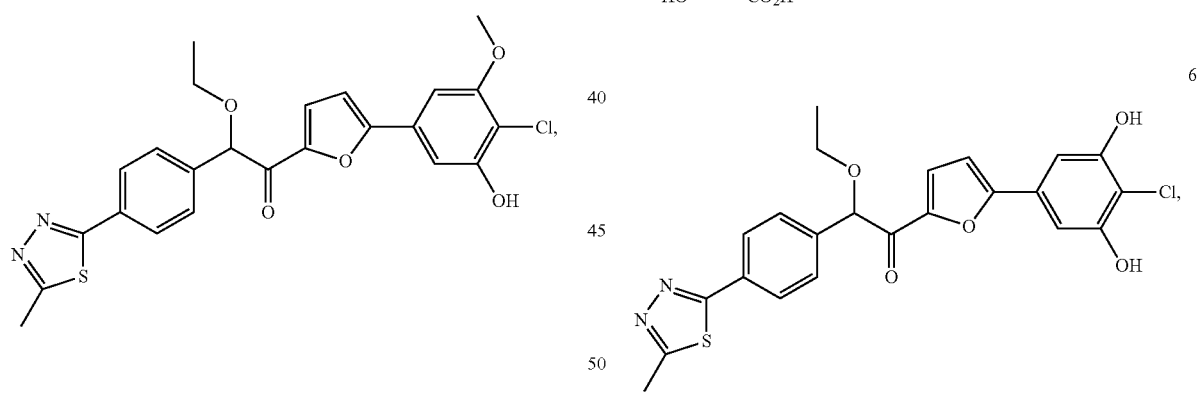

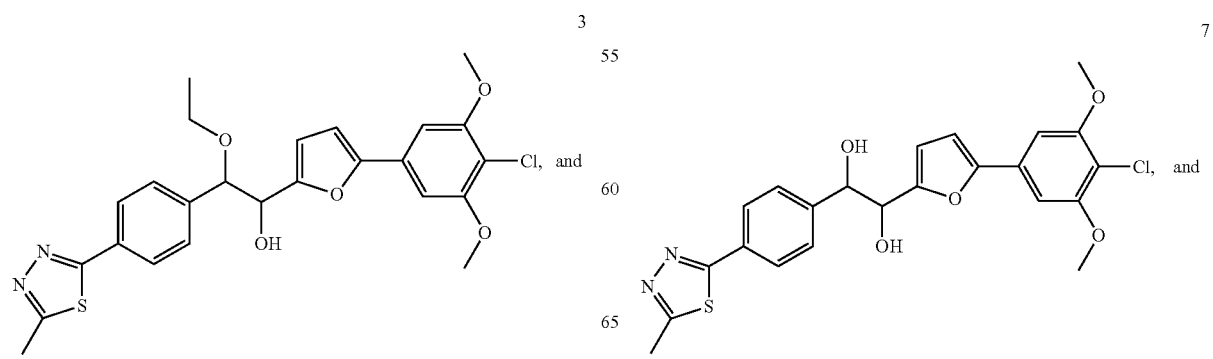

-continued

8

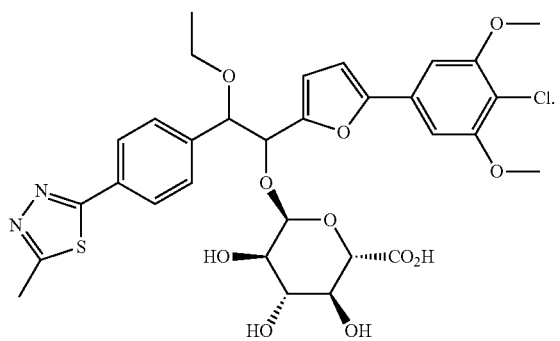

In another embodiment, the compounds of the present invention have purities of at least about 99.5%. In a further embodiment, the compounds of the present invention have purities of at least about 99%. In still further embodiment, the compounds of the present invention have purities of at least about 98.5%. In still other embodiments, the compounds of the present invention have purities of at least about 98%. In yet other embodiments, the compounds of the present invention have purities of at least about 95%.

In one embodiment, the compounds of the present invention have higher aqueous solubilities than previously synthesized PDE10 inhibitors, for example those of U.S. Pat. Nos. 8,343,970 and 8,685,975, yet have similar levels of biological activity. In some embodiments, the compounds of the present invention have aqueous solubilities at least about 1.5-fold higher than previously synthesized PDE10 inhibitors. In some embodiments, the compounds of the present invention have aqueous solubilities at least about 2-fold higher than previously synthesized PDE10 inhibitors. In some embodiments, the compounds of the present invention have aqueous solubilities at least about 5-fold higher than previously synthesized PDE10 inhibitors. In some embodiments, the compounds of the present invention have aqueous solubilities at least about 10-fold higher than previously synthesized PDE10 inhibitors.

The compounds of the present invention may generally be utilized in the form of a free base. Alternatively, the compounds of this invention may be used in the form of an acid addition salt. Acid addition salts of the free base form of the compounds of the present invention may be prepared by methods well known in the art, and may be formed from reaction of the free base with organic or inorganic acids. Suitable organic acids include, for example, maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include, for example, hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein, for example, the hydroxys are bonded to any group that, when the compound is administered to a patient, cleaves to re-form the hydroxy. Thus, representative examples of prodrugs include (but are not limited to) acetate, formate and benzoate derivatives of alcohol and amine functional groups of the compounds of structure (I). Alcohol protecting group chemistry is well known in the art. For example, in forming an acetate prodrug of an alcohol, one may react the alcohol with an acyl chloride and a base.

The invention disclosed herein is also meant to encompass all pharmaceutically acceptable compounds of isolated or substantially pure compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

With regard to stereoisomers, the compounds of structure (I) have a chiral center, and may occur as racemates, racemic mixtures, or as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment of the invention, pharmaceutical compositions containing one or more isolated or substantially pure compounds of structure (I) are disclosed. For the purposes of administration, the compounds of the present invention may be formulated as pharmaceutical compositions. Pharmaceutical compositions of the present invention comprise one or more compounds of the present invention and at least one pharmaceutically acceptable carrier and/or diluent. The PDE10 inhibitor is present in the composition in an amount which is effective to treat a particular disorder—that is, in an amount sufficient to achieve desired PDE10 inhibition, and preferably with acceptable toxicity to the warm-blooded animal. Typically, the pharmaceutical compositions of the present invention may include a PDE10 inhibitor in an amount from 0.1 mg to 250 mg per dosage depending upon the route of administration, and more typically from 1 mg to 60 mg. Appropriate concentrations and dosages can be readily determined by one skilled in the art.

In general terms, a typical daily dosage might range from about 1 µg/kg to 100 mg/kg, preferably 0.01-100 mg/kg, more preferably 0.1-70 mg/kg, depending on the type and severity of the disease whether, for example, by one or more separate administrations. For repeated administrations over several days or longer, depending on the condition, the treatment is sustained until a desired suppression of disease symptoms occurs. However, other dosage regimens may be useful. The progress of this therapy can be monitored by standard techniques and assays. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a PDE10 inhibitor, diluents, dispersing and surface active agents, binders, and lubricants. One skilled in this art may further formulate the PDE10 inhibitor in an appropriate manner, and in accordance with accepted practices, such as those disclosed in Remington's Pharmaceutical Sciences, Gennaro, Ed., Mack Publishing Co., Easton, Pa. 1990.

In another embodiment, the present invention provides a method for treating diseases such as (but not limited to) psychotic disorders, anxiety disorders, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, post-traumatic stress disorders, drug-induced psychosis, panic disorders, obsessive-compulsive disorders, attention-deficit disorders, disruptive behavior disorders, autism, depression, dementia, cognitive disorders, epilepsy, insomnias and multiple sclerosis as discussed above. Such methods include administering a compound of the present invention to a warm-blooded animal in an amount sufficient to treat the condition. In this context, "treat" includes prophylactic administration. Such methods include systemic administration of a PDE10 inhibitor of this invention, preferably in the form of a pharmaceutical composition as discussed above. As used herein, systemic administration includes oral and parenteral methods of administration, including subcutaneous, intramuscular, intracranial, intraorbital, ophthalmic, intraventricular, intracapsular, intraarticular, intraspinal, intracisternal, intraperitoneal, intranasal, aerosol, intravenous, intradermal, inhalational, transdermal, transmucosal, and rectal administration.

For oral administration, suitable pharmaceutical compositions of PDE10 inhibitors include powders, granules, pills, tablets, and capsules as well as liquids, syrups, suspensions, and emulsions. These compositions may also include flavorants, preservatives, suspending, thickening and emulsifying agents, and other pharmaceutically acceptable additives and excipients. For parenteral administration, the compounds of the present invention can be prepared in aqueous injection solutions which may contain, in addition to the PDE10 inhibitor, buffers, antioxidants, bacteriostats, and other additives and excipients commonly employed in such solutions. Compositions of the present invention may be carried in a delivery system to provide for sustained release or enhanced uptake or activity of the therapeutic compound, such as a liposomal or hydrogel system for injection, a microparticle, nanoparticle, or micelle system for oral or parenteral delivery, or a staged capsule system for oral delivery.

In a further advantage of the present invention, compounds of structure (I) are expected to avoid or reduce metabolic side effects associated with conventional antipsychotics, in particular the incidence of therapeutically induced obesity. For example, chronic use of olanzapine (Zyprexa®), the most widely prescribed medication to treat schizophrenia, and related atypical antipsychotics is associated with significant metabolic side effects including obesity and associated conditions such as diabetes.

In animals, subchronic treatment with olanzapine stimulates food intake and increases body weight, consistent with human situations. Furthermore, olanzapine acutely lowers blood leptin levels. Leptin is a satiety hormone produced from adipose tissues, and decrease of leptin level stimulates appetite. It is theorized that olanzapine could stimulate food intake at least partly by reducing leptin levels. Acute administration of olanzapine also changes the animal's response in glucose and insulin levels in glucose tolerance tests, which may also be directly linked to olanzapine's effect in food intake and body weight gain. Examination of the acute effect of PDE10 inhibitors of the present invention on metabolism, such as leptin, insulin and glucose changes during a metabolic challenge in standard animal models, as well as the chronic effect of PDE10 inhibitors of the present invention in food intake, body weight and energy homeostasis, in comparison with olanzapine should provide evidence to the pharmaceutical advantage of PDE10 inhibitors as antipsychotics in terms of less side-effect concerns.

The compositions of the present invention may be administered in combination with one or more additional therapeutic agents, in combination or by concurrent or sequential administration. Suitable additional agents (i.e., adjuvants) may include typical antipsychotics that block dopamine-$D_2$ receptors and serotonin $5HT_2$ receptors, e.g., haloperidol, fluphenazine, chlorpromazine, and atypical antipsychotics, e.g., clozapine, olanzapine, risperidone, quetiapine, ziprasidone.

Compounds of this invention may be assayed to determine their $IC_{50}$ values by a modification of the two-step method of Thompson and Appleman (*Biochemistry* 10; 311-316; 1971). In short, cAMP is spiked with ($^3$H)cAMP and incubated with PDE10 and various concentrations of a compound of structure (I). After the appropriate incubation time, the reaction is terminated by heating. The mixture is then subjected to treatment with snake venom phosphatase. The phosphatase hydrolyzes any AMP in the mixture, but leaves unreacted cAMP intact. Thus, by separating cAMP from the mixture and determining its concentration (by radiography), the percent of inhibition can be determined. $IC_{50}$ values can be calculated by performing the experiment at several concentrations using standard graphical means. A detailed description of the actual technique used for $IC_{50}$ assays as set forth in following Examples. To this end, PDE10 inhibitors of the invention have an $IC_{50}$ of 100 μM or less, generally less than 10 μM, and typically less than 1 μM.

The compounds of the present invention may be prepared by known organic synthesis techniques, including the methods described in more detail in the following examples. The following examples are provided for purposes of illustration, not limitation.

EXAMPLES

Reagents were purchased from the commercial sources and were used as received. $^1$H NMR spectra were obtained on a Bruker AVANCE 300 spectrometer at 300 MHz and a Bruker AVANCE 400 spectrometer at 400 MHz with tetramethylsilane used as an internal reference. $^{13}$C NMR spectra were obtained on a Bruker AVANCE 400 spectrometer at 100 MHz with the solvent peak used as the reference. Thin-layer chromatography (TLC) was performed using Whatman No. 4500-101 (Diamond No. MK6F silica-gel 60 Å) plates. Visualization of TLC plates was performed using UV light (254 nm). The mass spectra were obtained on a Finnigan LCQ-DUO spectrometer using electrospray ionization. HPLC analyses were performed on an Agilent 1100 Series instrument. Impurities are expressed as % AUC by HPLC and are non-validated.

Example 1

1-[5-(4-chloro-3-hydroxy-5-methoxyphenyl)furan-2-yl]-2-ethoxy-2-[4-(5-methyl-1,3,4-thiadiazol-yl)phenyl]ethanone (Compound 1)

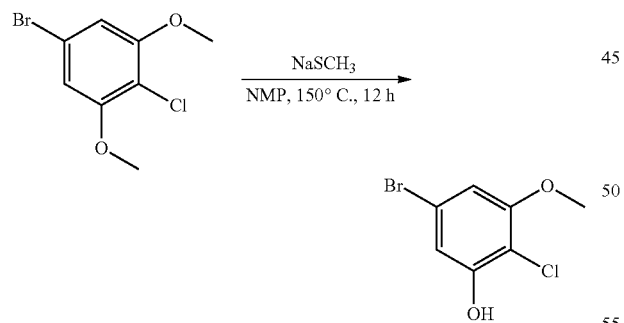

A stirred solution of 5-bromo-2-chloro-1,3-dimethoxybenzene (20.0 g, 79.5 mmol) in NMP (150 mL) was charged with NaSMe (6.20 g, 87.5 mmol) at room temperature. The reaction mixture was stirred for 12 hours at 150° C. The reaction mixture was cooled to room temperature. HCl (2 N, 100 mL) was added to the reaction mixture and were extracted with EtOAc (2×300 mL). The combined organic layers were washed with water (200 mL) and brine (200 mL). The organic layers were dried over anhydrous $Na_2SO_4$ and were concentrated under reduced pressure to afford crude product. The crude product was purified by column chromatography (5% EtOAc/hexanes) to afford 5-bromo-2-chloro-3-methoxyphenol (4.50 g, 24%) as a pale yellow thick liquid.

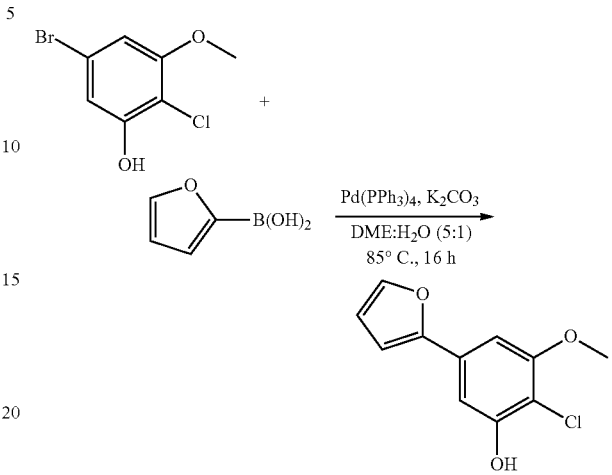

A stirred solution of 5-bromo-2-chloro-3-methoxyphenol (3.60 g, 15.1 mmol) in DME:water (5:1, 18 mL) was treated with furan-2-ylboronic acid (3.38 g, 30.3 mmol), $K_2CO_3$ (3.14 g, 22.7 mmol) at room temperature and was purged with $N_2$ gas for 30 min. $Pd(PPh_3)_4$ (1.75 g, 1.51 mmol) was added to the reaction mixture, which was placed in a sealed tube and was stirred for 16 hours at 85° C. The reaction mixture was cooled to room temperature. Water (20.0 mL) was added to the reaction mixture and was extracted with EtOAc (2×50 mL). The combined organic layers were washed with brine (20 mL). The organic layers were dried over anhydrous $Na_2SO_4$ and were concentrated under reduced pressure to afford crude. The crude product was purified by column chromatography (15% EtOAc/hexanes) to afford 2-chloro-5-(furan-2-yl)-3-methoxyphenol (3.00 g, 88%) as a colorless thick liquid.

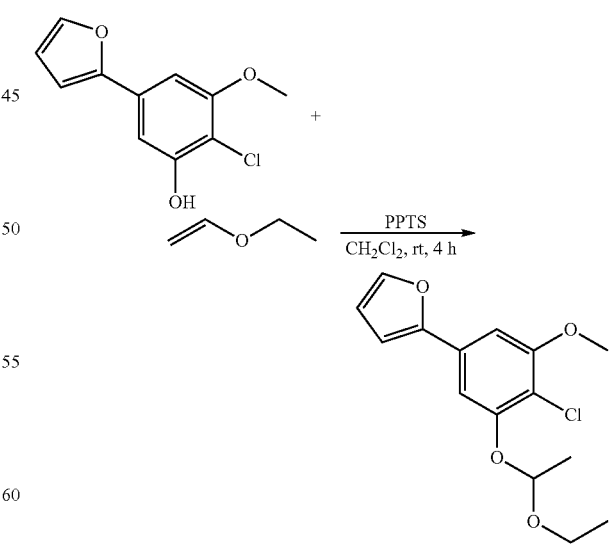

A stirred solution of 2-chloro-5-(furan-2-yl)-3-methoxyphenol (3.00 g, 13.4 mmol) in $CH_2Cl_2$ (20 mL) was charged with PPTS (1.00 g, 4.00 mmol) and ethyl vinyl ether (4.80 g, 6.69 mmol) at 0° C. The reaction mixture was stirred for 4 hours at room temperature. The reaction mixture was diluted with CH$_2$Cl$_2$ (50 mL) and water (10 mL). The organic layers were separated, washed with water (30 mL) and brine (30 mL). The organic layers were dried over anhydrous Na$_2$SO$_4$ and were concentrated under reduced pressure to afford crude product. The crude product was purified by column chromatography (5% EtOAc/hexanes) to afford 2-(4-chloro-3-(1-ethoxyethoxy)-5-methoxyphenyl)furan (3.00 g, 77%) as a light red liquid.

hexanes) to afford 1-(5-(4-chloro-3-(1-ethoxyethoxy)-5-methoxyphenyl)furan-2-yl)-2-ethoxy-2-(4-(5-methyl-1,3,4-thiadiazol-2-yl)phenyl)ethan-1-one (2.00 g, 41%) as a yellow solid. See U.S. Pat. No. 8,343,970 for the synthesis of 2-ethoxy-N-methoxy-N-methyl-2-(4-(5-methyl-1,3,4-thiadiazol-2-yl)phenyl)acetamide.

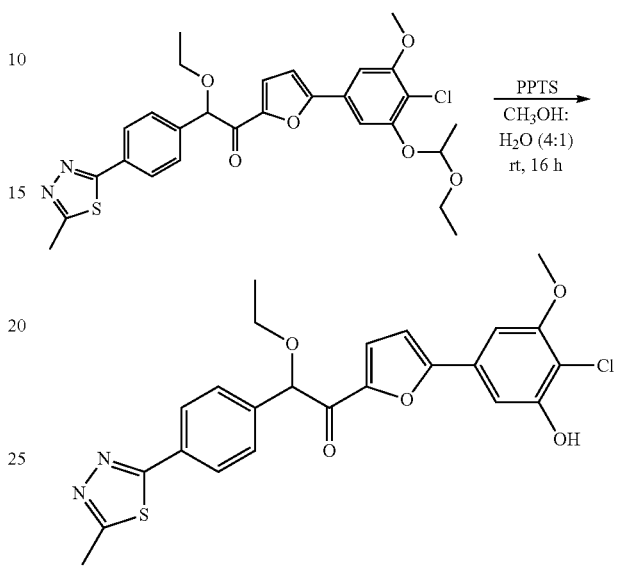

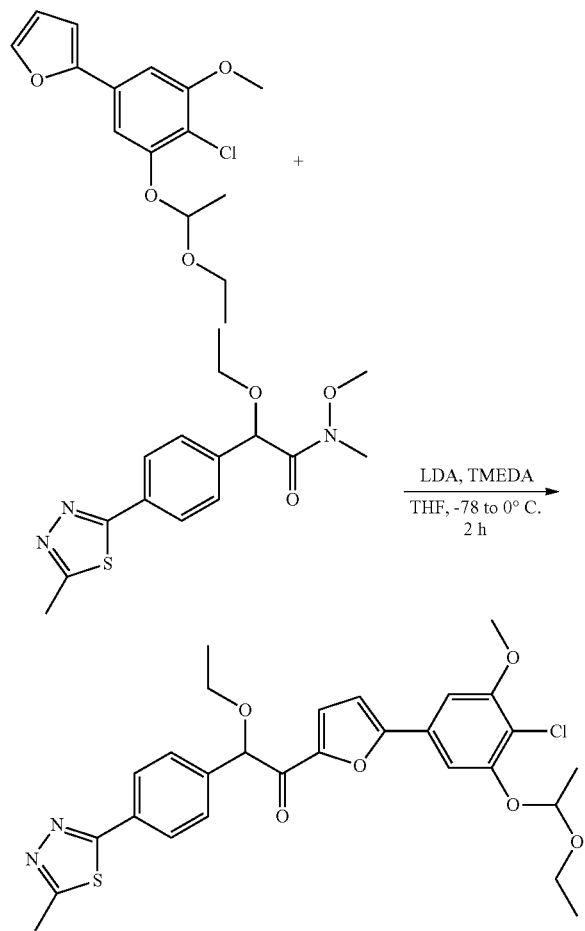

A stirred solution of 1-(5-(4-chloro-3-(1-ethoxyethoxy)-5-methoxyphenyl)furan-2-yl)-2-ethoxy-2-(4-(5-methyl-1,3,4-thiadiazol-2-yl)phenyl)ethan-1-one (2.00 g, 3.59 mmol) in MeOH:water (4:1, 25 mL) was charged with PPTS (0.09 g, 0.359 mmol) at room temperature and was stirred for 16 hours. When TLC analysis showed complete consumption of the starting material, the reaction mixture was concentrated, dissolved in CH$_2$Cl$_2$ (30 mL) and was washed with water (2×10 mL). The organic layer was washed with brine (10 mL). The organic layer was dried over anhydrous Na$_2$SO$_4$ and was concentrated under reduced pressure to afford crude product. The crude product was purified by column chromatography (60% EtOAc/hexanes) to afford 1-(5-(4-chloro-3-hydroxy-5-methoxyphenyl)furan-2-yl)-2-ethoxy-2-(4-(5-methyl-1,3,4-thiadiazol-2-yl)phenyl)ethan-1-one (0.80 g, 47%) as a yellow solid. MS: m/z 485.1 [M+H]$^+$.

A stirred solution of 2-(4-chloro-3-(1-ethoxyethoxy)-5-methoxyphenyl)furan (3.00 g, 10.1 mmol) in THF (150 mL) was charged with LDA (2 M in THF; 5.57 mL, 11.1 mmol) dropwise over 10 min followed by TMEDA (1.29 g, 11.1 mmol) dropwise over 2 min at −78° C. under argon atmosphere. The reaction mixture was stirred at the same temperature for 1 hour. 2-Ethoxy-N-methoxy-N-methyl-2-(4-(5-methyl-1, 3, 4-thiadiazol-2-yl)phenyl)acetamide (3.26 g, 10.1 mmol) in THF (50.0 mL) was added dropwise over 5 min and was stirred for 30 min at the same temperature. The temperature was raised to 0° C. and was stirred for 30 min at that temperature. When TLC analysis showed complete consumption of the starting material, the reaction mixture was quenched with water (50 mL) and was extracted with EtOAc (2×150 mL). The combined organic layers were washed with brine (100 mL). The organic layers were dried over anhydrous Na$_2$SO$_4$ and were concentrated under reduced pressure to afford crude product. The crude product was purified by column chromatography (40% EtOAc/

Example 2

1-(5-(4-chloro-3,5-dimethoxyphenyl)furan-2-yl)-2-ethoxy-2-(4-(5-(hydroxymethyl)-1,3,4-thiadiazol-2-yl)phenyl)ethan-1-one (Compound 2)

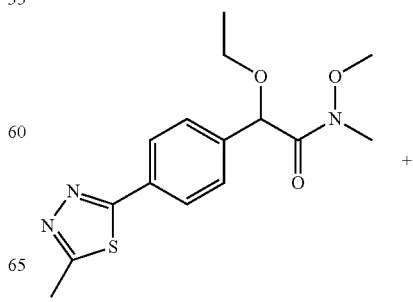

-continued

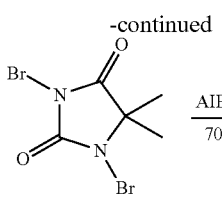

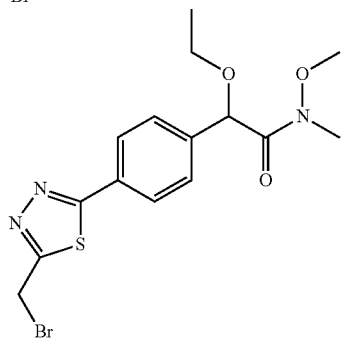

A stirred solution of 2-ethoxy-N-methoxy-N-methyl-2-(4-(5-methyl-1,3,4-thiadiazol-2-yl)phenyl)acetamide (10.0 g, 31.1 mmol) in DMF (100 mL) was charged with 1,3-dibromo-5,5-dimethylhydantoin (8.90 g, 31.1 mmol) at room temperature and was stirred for 1 hour at 70° C. AIBN (2.50 g, 15.5 mmol) was added to the reaction mixture at 70° C. and was stirred for 3 hours at 100° C. When TLC analysis showed complete consumption of the starting material, the reaction mixture was cooled to room temperature, slowly poured into ice-cold water (500 mL) and was extracted with EtOAc (2×500 mL). The organic layers were dried over anhydrous Na$_2$SO$_4$ and were concentrated under reduced pressure to afford crude product. The crude product was purified by column chromatography (40% EtOAc/hexanes) to afford 2-(4-(5-(bromomethyl)-1,3,4-thiadiazol-2-yl)phenyl)-2-ethoxy-N-methoxy-N-methylacetamide (3.36 g, 27%) as a pale yellow solid.

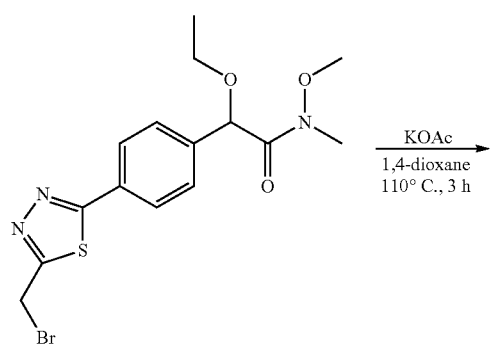

A stirred solution of 2-(4-(5-(bromomethyl)-1,3,4-thiadiazol-2-yl)phenyl)-2-ethoxy-N-methoxy-N-methylacetamide (2.00 g, 4.99 mmol) in 1,4-dioxane (20 mL) was charged with KOAc (0.98 g, 9.99 mmol) at room temperature and was stirred at 110° C. for 3 hours. When TLC analysis showed complete consumption of the starting material, the reaction mixture was concentrated; water (20 mL) was added and was extracted with EtOAc (2×50 mL). The organic layers were dried over anhydrous Na$_2$SO$_4$ and were concentrated under reduced pressure to afford crude. The crude product was purified by column chromatography (40% EtOAc/hexanes) to afford 2-(4-(5-(acetoxymethyl)-1,3,4-thiadiazol-2-yl)phenyl)-2-ethoxy-N-methoxy-N-methylacetamide (1.13 g, 60%) as a liquid.

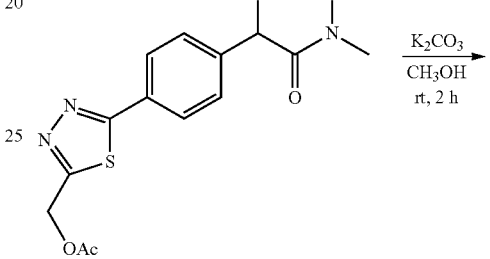

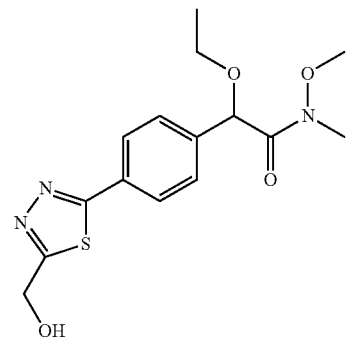

A stirred solution of 2-(4-(5-(acetoxymethyl)-1,3,4-thiadiazol-2-yl)phenyl)-2-ethoxy-N-methoxy-N-methylacetamide (0.50 g, 1.31 mmol) in MeOH (10 mL) was charged with K$_2$CO$_3$ (0.27 g, 1.96 mmol) at room temperature. The reaction mixture was stirred for 2 hours at the same temperature. When TLC analysis showed complete consumption of the starting material, water (30 mL) was added and was extracted with EtOAc (2×20 mL). The combined organic layers were washed with water (20 mL) and brine (20 mL). The organic layers were dried over anhydrous Na$_2$SO$_4$ and were concentrated under reduced pressure to afford crude product. The crude product was triturated with MTBE to afford 2-ethoxy-2-(4-(5-(hydroxymethyl)-1,3,4-thiadiazol-2-yl)phenyl)-N-methoxy-N-methylacetamide (0.20 g, 46%) as a yellow solid.

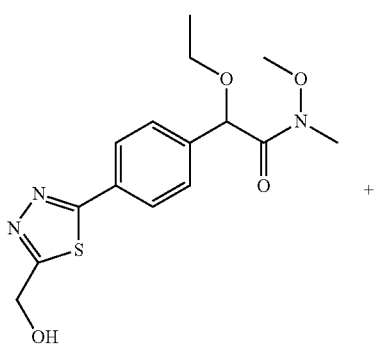

+

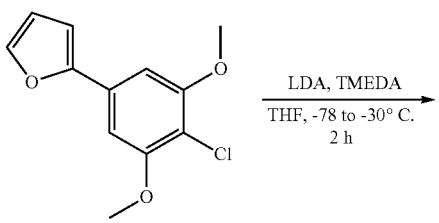

LDA, TMEDA
———————→
THF, −78 to −30° C.
2 h

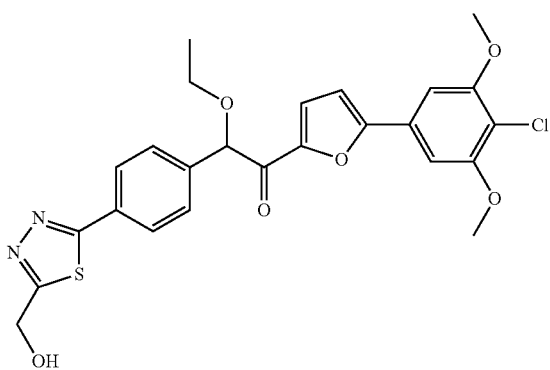

2

A stirred solution of 2-(4-chloro-3,5-dimethoxyphenyl) furan (1.60 g, 6.73 mmol) in THF (30.0 mL) was charged with LDA (2 M in THF) (3.70 mL, 7.40 mmol) dropwise over 2 min followed by TMEDA (0.86 g, 7.40 mmol) dropwise over 2 min at −78° C. The reaction mixture was stirred for 1 hour at the same temperature. 2-Ethoxy-2-(4-(5-(hydroxymethyl)-1,3 adiazol-2-yl)phenyl)-N-methoxy-N-methylacetamide (2.50 g, 7.40 mmol) in THF (20 mL) was added dropwise over 2 min at the same temperature. The temperature was slowly raised to −30° C. and was stirred for 1 hour at that temperature. When TLC analysis showed complete consumption of the starting material, the reaction mixture was quenched with water (20 mL) and was extracted with EtOAc (2×50 mL). The organic layers were dried over anhydrous $Na_2SO_4$ and were concentrated under reduced pressure to afford crude product. The crude product was purified by column chromatography (30% EtOAc/hexanes) to afford 1-(5-(4-chloro-3,5-dimethoxyphenyl)furan-2-yl)-2-ethoxy-2-(4-(5-(hydroxymethyl)-1,3,4-thiadiazol-2-yl)phenyl)ethan-1-one (0.29 g, 8%) as a yellow solid (see Attachments 5-9 for analytical data). MS: m/z 515.2 $[M+H]^+$.

Example 3

(2S,3S,4S,5R,6R)-6-(2-chloro-5-(5-(2-ethoxy-2-(5-methyl-1,3,4-thiadiazol-2-yl)phenyl)acetyl)furan-2-yl-methoxyphenoxy)-3,4,5-trihydroxytetrahydro-2H-pyran-2-carboxylic acid (Compound 3)

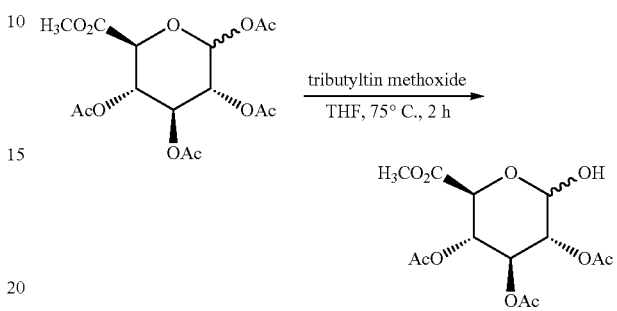

tributyltin methoxide
————————→
THF, 75° C., 2 h

A stirred solution of 6-(methoxycarbonyl)tetrahydro-2H-pyran-2,3,4,5-tetrayl tetraacetate as drawn (5.50 g, 14.6 mmol) in THF (50 mL) was charged with tributyltin methoxide (4.69 g, 14.6 mmol) at room temperature. The reaction mixture was stirred for 2 hours at 75° C. When TLC analysis showed complete consumption of the starting material, the reaction mixture was cooled to room temperature and was quenched with HCl (2 N, 20 mL). The aqueous layer was extracted with EtOAc (2×100 mL). The combined organic layers were washed with water (50 mL) and brine (50 mL). The organic layers were dried over $Na_2SO_4$ and were concentrated under reduced pressure. The residue was purified by column chromatography (50% EtOAc/hexanes) to afford (3R,4S,5S,6S)-2-hydroxy-6-(methoxycarbonyl)tetrahydro-2H-pyran-3,4,5-triyl triacetate (3.00 g, 63%) as a colorless liquid.

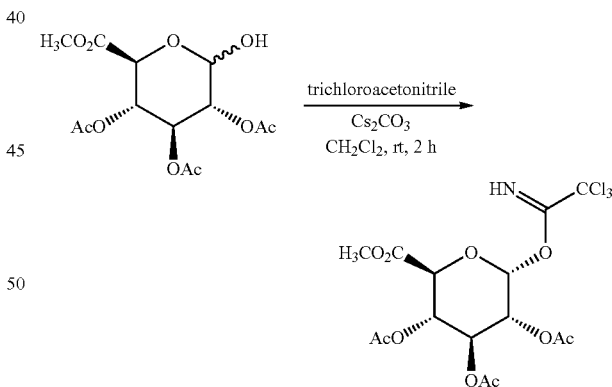

trichloroacetonitrile
————————→
$Cs_2CO_3$
$CH_2Cl_2$, rt, 2 h

A stirred solution of (3R,4S,5S,6S)-2-hydroxy-6-(methoxycarbonyl)tetrahydro-2H-pyran-3,4,5-triyl triacetate (3.00 g, 8.98 mmol) in $CH_2Cl_2$ (30 mL) was charged with trichloroacetonitrile (12.9 g, 89.8 mmol) and $Cs_2CO_3$ (1.40 g, 4.49 mmol) at room temperature. The reaction mixture was stirred at same temperature for 2 hours. When TLC analysis showed complete consumption of the starting material, the reaction mixture was diluted with $CH_2Cl_2$ (50 mL), washed with aqueous $NaHCO_3$ solution (2×20 mL), water (20 mL) and brine (20 mL). The organic layer was dried over anhydrous $Na_2SO_4$ and was concentrated under reduced pressure to afford crude. The crude product was purified by column chromatography (20% EtOAc/hexanes) to afford (2S,3S,4S,5R,6R)-2-(methoxycarbonyl)-6-(2,2,2-trichloro-1-iminoethoxy)tetrahydro-2H-pyran-3,4,5-triyl triacetate (2.00 g, 48%) as a colorless liquid.

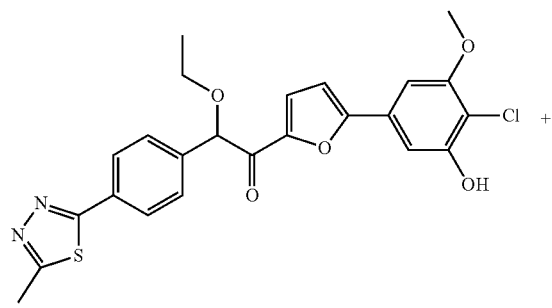

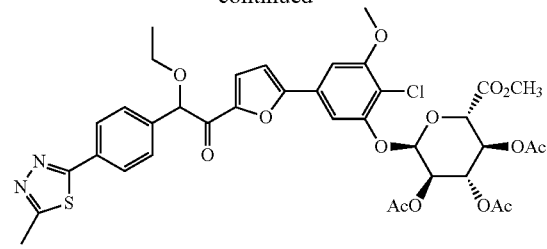

A suspension of 1-(5-(4-chloro-3-hydroxy-5-methoxyphenyl)furan-2-yl)-2-ethoxy-2-(4-(5-methyl-1,3,4-thiadiazol-2-yl)phenyl)ethan-1-one (0.15 g, 0.300 mmol), (2S,3S, 4S,5R,6R)-2-(methoxycarbonyl)-6-(2,2,2-trichloro-1-iminoethoxy)tetrahydro-2H-pyran-3,4,5-triyl triacetate (0.222 g, 0.460 mmol) and dry 4 Å molecular sieves (0.25 g) in $CH_2Cl_2$ (10 mL) at room temperature under argon atmosphere was stirred for 1 hour. The reaction mixture was cooled to −78° C. and $BF_3.OEt_2$ (0.012 g, 0.09 mmol) was added dropwise over 20 min and stirred for 1 hour at the same temperature. The reaction mixture was stirred for 16 hours at room temperature. The reaction mixture was diluted with $CH_2Cl_2$ (15 mL). The organic layer was filtered through a Celite® bed. The organic layer was washed with aqueous $NaHCO_3$ (15 mL), water (10 mL) and brine (10 mL). The organic layer was dried over anhydrous $Na_2SO_4$ and was concentrated under reduced pressure to afford the crude product. The crude product was purified by column chromatography (60% EtOAc/hexanes) to afford (2R,3R,4S,5S, 6S)-2-(2-chloro-5-(5-(2-ethoxy-2-(4-(5-methyl-1,3,4-thiadiazol-2-yl)phenyl)acetyl)furan-2-yl)-3-methoxyphenoxy)-6-(methoxycarbonyl)tetrahydro-2H-pyran-3,4,5-triyl triacetate (0.10 g, 40%) with a light yellow solid.

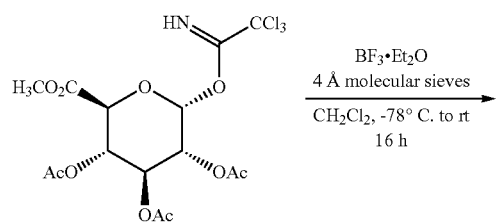

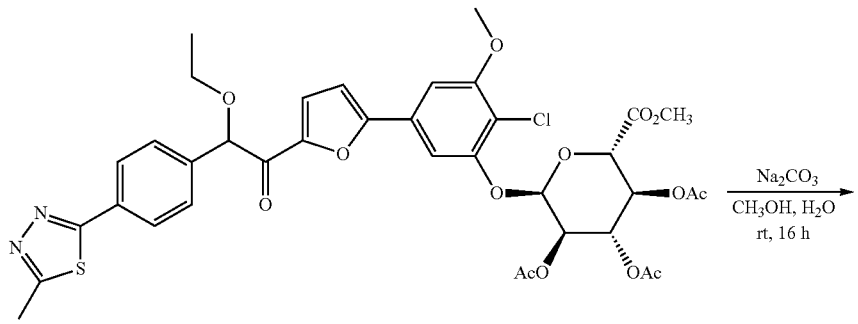

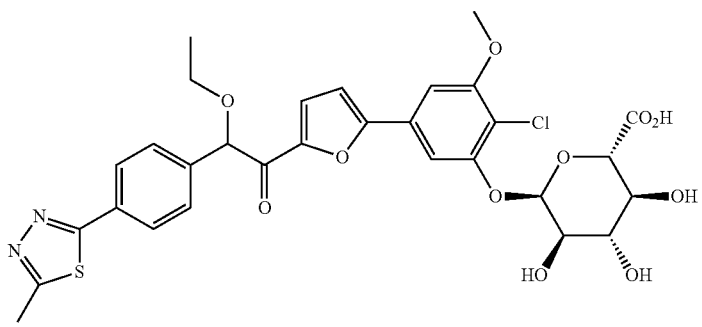

A stirred solution of (2R,3R,4S,5S,6S)-2-(2-chloro-5-(5-(2-ethoxy-2-(4-(5-methyl-1,3,4-thiadiazol-2-yl)phenyl)acetyl)furan-2-yl)-3-methoxyphenoxy)-6-(methoxycarbonyl) tetrahydro-2H-pyran-3,4,5-triyl triacetate (0.10 g, 0.125 mmol) in MeOH (3.0 mL) was charged with Na₂CO₃ (0.02 g, 0.250 mmol) in water (0.50 mL) at room temperature and was stirred for 16 hours at that temperature. When TLC analysis showed complete consumption of the starting material, the reaction mixture was diluted with MeOH (5.0 mL) and the pH was adjusted to 6 with Amberlyst-15 ion exchange resin. The reaction mixture was filtered. The filtrate was concentrated to afford crude residue which was purified with prep HPLC. Prep fractions (Acetonitrile and water) were concentrated under vacuum below 40° C. to afford (2S,3S,4S,5R,6R)-6-(2-chloro-5-(5-(2-ethoxy-2-(4-(5-methyl-1,3,4-thiadiazol-2-yl)phenyl)acetyl)furan-2-yl)-3-methoxyphenoxy)-3,4,5-trihydroxytetrahydro-2H-pyran-2-carboxylic acid (0.06 g, 70%) as a yellow solid. MS: m/z 659.1 [M+H]⁺.

Prep HPLC Method

Column: Sunfire OBD, C18, 10 μm, 30×250 mm
Mobile Phase: ACN and 0.1% TFA in Water

| Time | Percent A (ACN) | Percent B (0.1% TFA in Water) |
| --- | --- | --- |
| 0.00 | 20 | 80 |
| 1.00 | 20 | 80 |
| 18.0 | 55 | 45 |
| 19.0 | 95 | 5 |
| 23.0 | 95 | 5 |
| 23.2 | 20 | 80 |
| 25.0 | 20 | 80 |

Example 4

1-(5-(4-chloro-3,5-dimethoxyphenyl)furan-2-yl)-2-ethoxy-2-(4-(5-methyl-1,3,4-thiadiazol-2-yl)phenyl)ethan-1-ol (Compound 4)

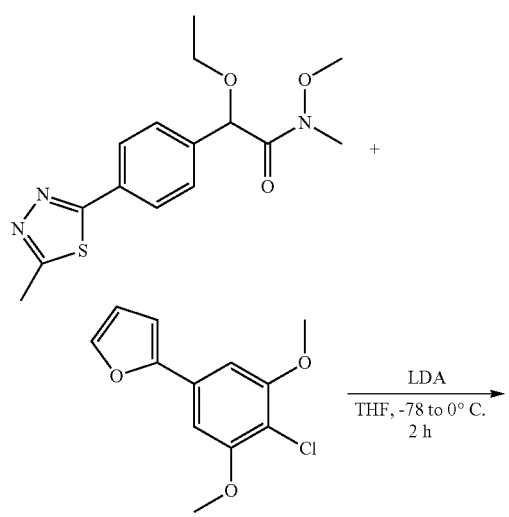

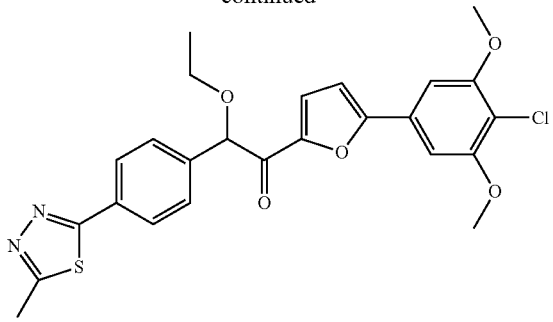

A stirred solution of 2-(4-chloro-3,5-dimethoxyphenyl)furan (1.00 g, 4.20 mmol) in THF (120 mL) was charged with LDA (2 M in THF, 2.31 mL, 4.62 mmol) dropwise over 5 min at −78° C. under argon atmosphere and was stirred for 1 hour at the same temperature. 2-Ethoxy-N-methoxy-N-methyl-2-(4-(5-methyl-1,3,4-thiadiazol-2-yl)phenyl)acetamide (1.40 g, 4.20 mmol) in THF (30 mL) was added over 15 min and was stirred for 15 min at the same temperature. The temperature was slowly raised to 0° C. and the reaction mixture was stirred for 30 min. When TLC analysis showed complete consumption of the starting material, the reaction mixture was quenched with HCl (1 N, 10 mL) and was extracted with EtOAc (2×50 mL). The combined organic layers were washed with water (50 mL) and brine (100 mL). The organic layers were dried over anhydrous Na₂SO₄ and were concentrated under reduced pressure to obtain crude product, which was purified by column chromatography using 60% EtOAc/n-hexane to afford 1-(5-(4-chloro-3,5-dimethoxyphenyl)furan-2-yl)-2-ethoxy-2-(4-(5-methyl-1,3,4-thiadiol-2-yl)phenyl)ethan-1-one (0.80 g, 38%) as a yellow solid.

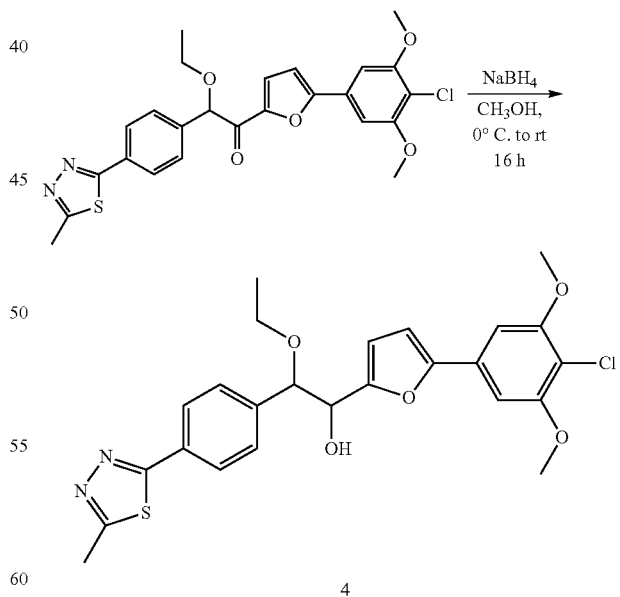

A stirred solution of 1-(5-(4-chloro-3,5-dimethoxyphenyl)furan-2-yl)-2-ethoxy-2-(4-(5-methyl-1,3,4-thiadiazol-2-yl)phenyl)ethan-1-one (0.50 g, 1.00 mmol) in MeOH (10 mL) was charged with NaBH₄ (0.019 g, 0.500 mmol) portionwise over 2 min at 0° C. and was stirred for 16 hours at room temperature. The reaction mixture was quenched with excess acetone (10 mL) and was stirred for additional 30 min. The reaction mixture was concentrated and the residue was subjected to column chromatography using 63% EtOAc in hexanes as eluent to afford pure 1-(5-(4-chloro-3,5-dimethoxyphenyl)furan-2-yl)-2-ethoxy-2-(4-(5-methyl-1,3,4-thiadiazol-2-yl)phenyl)ethan-1-ol (0.34 g, 68%) as a white solid. MS: m/z 501.1 [M+H]$^+$.

Example 5

Compound Assay

Solubilityy Assay

Solubility of each compound was measured by adding 4 µl of a 10 mM DMSO compound stock to 396 µl buffer (either a simulated Gastric Fluid pH 1.2 (0.2% NaCl, 0.7% HCl) or simulated Intestinal Fluid pH 7.5 (0.68% KHPO$_4$, pH with NaOH)). This was shaken for 24 hours at room temperature, spun at 14,000 rpm for 5 minutes, and the supernatant was transferred into a clean eppendorf tube. The absorption spectra of the compound-containing supernatant were measured from 220 to 400 nm and compared with the absorption spectra of a 10 µM acetonitrile stock of the same compound. The concentration of the compound in the supernatant was calculated by comparing the absorbance maximum of the compound in the simulated buffer to that in acetonitrile.

TABLE 1

Solubility test results

| Compound | 10 µM Acetonitrile | | pH 7.5 (IF) | | Conc. (µM) |
|---|---|---|---|---|---|
| | λmax | Abs. | λmax | Abs. | |
| A | 265 (P) | 0.25 | 265 (S) | 0.02 | <1 |
| 1 | 264 (P) | 0.28 | 265 (P) | 0.07 | 2.5 |
| 2 | 266 (P) | 0.28 | 268 (P) | 0.14 | 5.8 |
| 3 | 266 (P) | 0.23 | 264 (P) | 1.8 | 78.3 |
| 4 | 282 (P) | 0.48 | 271 (P) | 0.12 | 2.5 |

Detection limit is approximately 1 µM.
P = peak.
S = shoulder.
Compound A = 1-(5-(4-chloro-3,5-dimethoxyphenyl)furan-2-yl)-2-ethoxy-2-(4-(5-methyl-1,3,4-thiadiazol-2-yl)phenyl)ethan-1-one Example 6

Compound Assay

PDE10 Biochemical Assay

The phosphodiesterase (PDE) activity was measured using a scintillation proximity assay (SPA) with [$^3$H]-cGMP as the substrate. Purified PDE10 was stored in 40 mM Tris-Cl (pH 8.0)/100 mM NaCl/0.04% Tween-20/20% Glycerol/3 mM DTT and then used to prepare a 10×PDE solution in 50 mM Tris-Cl (pH 7.5)/8.3 mM MgCl$_2$/1.7 mM EGTA. Assays contained (final concentrations): 50 mM Tris-Cl (pH 7.5)/8.3 mM MgCl$_2$/1.7 mM EGTA/0.5 mg/ml BSA/1% DMSO and 2 ng PDE10 in a final volume of 0.1 mL. Inhibition was evaluated at 8 concentrations in duplicate. Reactions were initiated by addition of enzyme and were terminated after 20 minutes at 30° C. by the addition of 50 µl of SPA beads containing Zn$^{++}$. The mixture was shaken, allowed to settle for at least 1 hour, and counted in a Wallac plate counter. Results (net cpm) were fitted to a four parameter logistic model using Excel Solver®.

In the above assay, compounds of this invention are PDE10 inhibitors with an IC$_{50}$ of 100 µM or less, generally less than 10 and typically less than 1 µM. To this end, Compounds 1, 2, 3, and 4 for example, were found to have IC$_{50}$ values of less than or equal to 1 µM.

TABLE 2

IC$_{50}$ (nM)

| Compound | Average IC$_{50}$ (nM) |
|---|---|
| 1 | 37.7 |
| 2 | 1.3 |
| 3 | 652.5 |
| 4 | 127.1 |

It will be appreciated that, although specific embodiments of the invention have been described herein for purposes of illustration, various modifications may be made without departing from the spirit and scope of the invention. Accordingly, the invention is not limited except as by the appended claims.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims.

What is claimed is:

1. An isolated compound of the following structure (I):

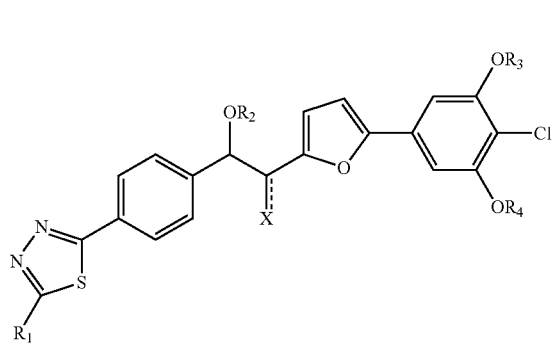

I or a pharmaceutically acceptable salt, stereoisomer, or solvate thereof, wherein:

R$_1$ is H, C$_{1-3}$ alkyl, hydroxy-C$_{1-3}$ alkyl, C$_{1-3}$ alkoxy, C$_{1-3}$ alkyl-O-glucuronidyl;

R$_2$ is H, ethyl, or glucuronidyl;

R$_3$ and R$_4$ are each independently H, C$_{1-3}$ alkyl, or glucuronidyl; and

X is =O, —OH or —O-glucuronidyl,
with the proviso that said compound of structure (I) is not:

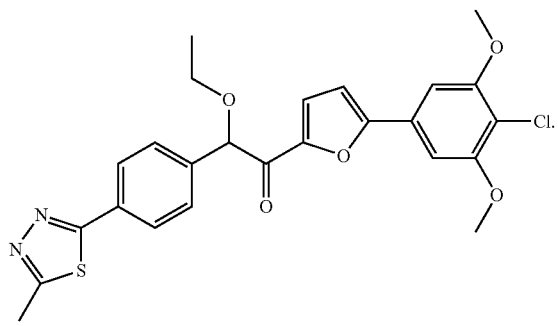 [SMILES: CCOC(C(=O)c1ccc(-c2cc(OC)c(Cl)c(OC)c2)o1)c1ccc(-c2nnc(C)s2)cc1]

2. The isolated compound of claim 1, wherein $R_1$ is methyl or hydroxymethyl.

3. The isolated compound of claim 1, wherein $R_2$ is ethyl.

4. The isolated compound of claim 1, wherein $R_3$ and $R_4$ are each independently H, methyl, or glucuronidyl.

5. The isolated compound of claim 1, wherein X is =O or —OH.

6. The isolated compound of claim 1, wherein the compound is selected from the group consisting of:

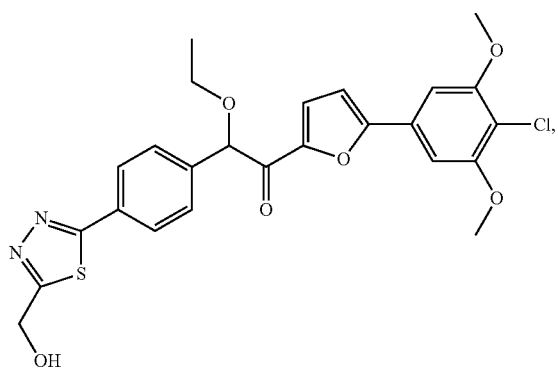

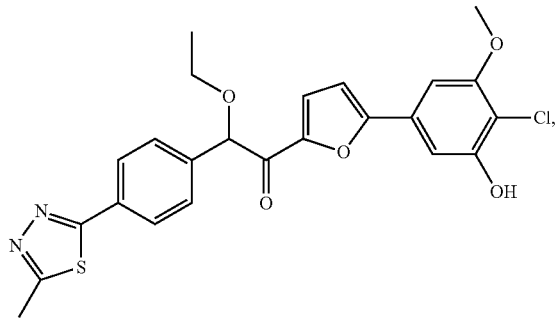

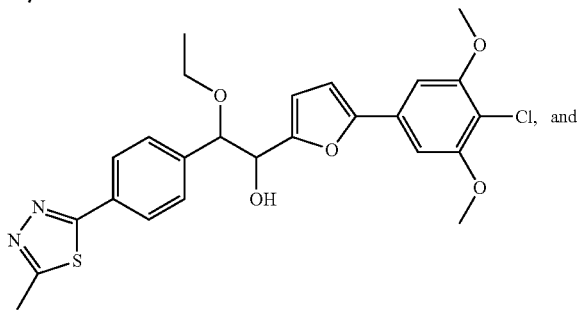

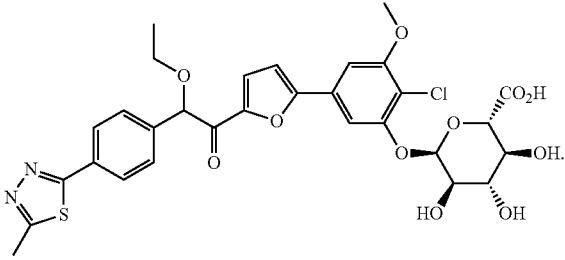

7. A compound of the following structure (I):

I or a pharmaceutically acceptable salt, stereoisomer, or solvate thereof, wherein:
  $R_1$ is H, $C_{1-3}$ alkyl, hydroxy-$C_{1-3}$ alkyl, $C_{1-3}$ alkoxy, $C_{1-3}$ alkyl-O-glucuronidyl;
  $R_2$ is H, ethyl, or glucuronidyl;
  $R_3$ and $R_4$ are each independently H, $C_{1-3}$ alkyl, or glucuronidyl; and
  X is =O, —OH or —O-glucuronidyl,
  with the proviso that said compound of structure (I) is not:

wherein the purity of the compound is 98% or higher.

8. The compound of claim 7, wherein $R_1$ is methyl or hydroxymethyl.

9. The compound of claim 7, wherein $R_2$ is ethyl.

10. The compound of claim 7, wherein $R_3$ and $R_4$ are each independently H, methyl, or glucuronidyl.

11. The compound of claim 7, wherein X is =O or —OH.

12. The compound of claim 7, wherein the compound is selected from the group consisting of:

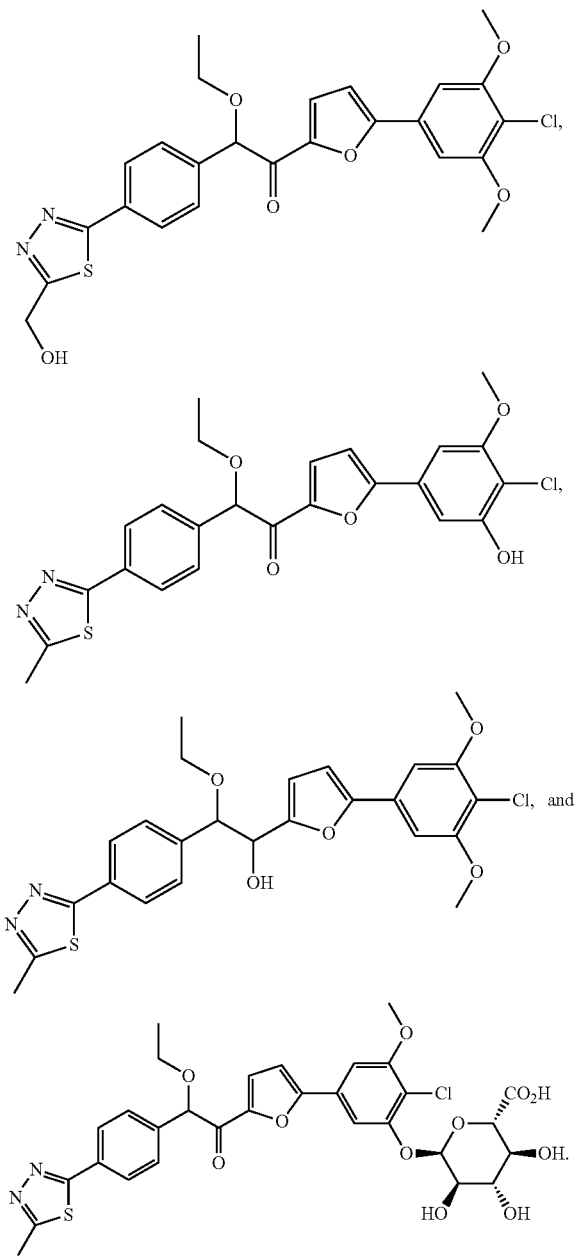

13. The compound of claim 7, wherein the purity of the compound is 98.5% or higher.

14. The compound of claim 7, wherein the purity of the compound is 99% or higher.

15. The compound of claim 7, wherein the purity of the compound is 99.5% or higher.

16. A pharmaceutical composition comprising the isolated compound of claim 1 and at least one pharmaceutically acceptable carrier or diluent.

17. A pharmaceutical composition comprising the compound of claim 7 and at least one pharmaceutically acceptable carrier or diluent.

18. A method for inhibiting PDE10 in a warm-blooded animal, comprising administering to the animal an effective amount of an isolated compound of claim 1 or a pharmaceutical composition of claim 16.

19. A method for inhibiting PDE10 in a warm-blooded animal, comprising administering to the animal an effective amount of a compound of claim 7 or a pharmaceutical composition of claim 17.

20. A method for treating neurological disorders in a warm-blooded animal in need thereof, comprising administering to the animal an effective amount of an isolated compound of claim 1 or a pharmaceutical composition of claim 16.

21. A method for treating neurological disorders in a warm-blooded animal in need thereof, comprising administering to the animal an effective amount of a compound of claim 7 or a pharmaceutical composition of claim 17.

22. The method of claim 20, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, posttraumatic stress disorders, drug-induced psychosis, panic disorders, obsessive-compulsive disorders, attention-deficit disorders, disruptive behavior disorders, autism, depression, dementia, epilepsy, insomnias, and multiple sclerosis.

23. The method of claim 22, wherein the neurological disorder is schizophrenia.

24. The method of claim 22, wherein the neurological disorder is post-traumatic stress disorder.

25. The method of claim 22, wherein the neurological disorder is Huntington's disease.

26. The method of claim 21, wherein the neurological disorder is selected from the group consisting of psychotic disorders, anxiety disorders, Parkinson's disease, Huntington's disease, Alzheimer's disease, encephalitis, phobias, epilepsy, aphasia, Bell's palsy, cerebral palsy, sleep disorders, pain, Tourette's syndrome, schizophrenia, delusional disorders, bipolar disorders, posttraumatic stress disorders, drug-induced psychosis, panic disorders, obsessive-compulsive disorders, attention-deficit disorders, disruptive behavior disorders, autism, depression, dementia, epilepsy, insomnias, and multiple sclerosis.

27. The method of claim 26, wherein the neurological disorder is schizophrenia.

28. The method of claim 26, wherein the neurological disorder is post-traumatic stress disorder.

29. The method of claim 26, wherein the neurological disorder is Huntington's disease.

* * * * *

UNITED STATES PATENT AND TRADEMARK OFFICE
CERTIFICATE OF CORRECTION

PATENT NO. : 9,879,002 B2
APPLICATION NO. : 15/136699
DATED : January 30, 2018
INVENTOR(S) : Gage et al.

It is certified that error appears in the above-identified patent and that said Letters Patent is hereby corrected as shown below:

In the Specification

| Column | Line | Error |
|---|---|---|
| 1 | 63 | "regulator fh1A" should read --fhlA-- |
| 4 | 20 | "=0 sub stituent" should read --=0 substituent-- |
| 11 | 39 | "1,3,4-THIADIAZOL-YL)PHENYL" should read --1,3,4-THIADIAZOL-2-YL)PHENYL-- |
| 15 | 24 | "in DIVIF (100 mL)" should read --in DMF (100 mL)-- |
| 17 | 52 | "(5-(hydroxymethyl)-1,3 adiazol-2-yl)phenyl)" should read --(5-(hydroxymethyl)-1,3,4-thiadiazol-2-yl)phenyl)-- |
| 18 | 3-6 | "(2S,3S,4S,5R,6R)-6-(2-chloro-5-(5-(2-ethoxy-2-(5-methyl-1,3,4-thiadiazol-2-yl)phenyl)acetyl)furan-2-yl-methoxyphenoxy)-3,4,5-trihydroxytetrahydro-2H-pyran-2-carboxylic acid (Compound 3)" should read --(2S,3S,4S,5R,6R)-6-(2-chloro-5-(5-(2-ethoxy-2-(4-(5-methyl-1,3,4-thiadiazol-2-yl)phenyl)acetyl)furan-2-yl)-3-methoxyphenoxy)-3,4,5-trihydroxytetrahydro-2H-pyran-2-carboxylic acid (Compound 3)-- |
| 20 | 20 | "$BF_3.OEt_2$" should read --$BF_3 \cdot OEt_2$-- |
| 23 | 46 | "methyl-1,3,4-thiadiazol-2-yl" should read --methyl-1,3,4-thiadiazol-2-yl-- |
| 24 | 5 | "less than 10 and typically less than 1 μM" should read --less than 10 μM, and typically less than 1 μM-- |

In the Claims

| | | |
|---|---|---|
| 24 | 63 | "$R_1$ is H, $C_{1-3}$ alkyl, hydroxy-$C_{1-3}$ alkyl, $C_{1-3}$ alkoxy, $C_{1-3}$ alkyl-O-glucuronidyl;" should read --$R_1$ is H, $C_{1-3}$ alkyl, hydroxy-$C_{1-3}$ alkyl, $C_{1-3}$ alkoxy, or $C_{1-3}$ alkyl-O-glucuronidyl;-- |

Signed and Sealed this
Eleventh Day of June, 2019

Andrei Iancu
*Director of the United States Patent and Trademark Office*

| 26 | 33 | "$R_1$ is H, $C_{1-3}$ alkyl, hydroxy-$C_{1-3}$ alkyl, $C_{1-3}$ alkoxy, $C_{1-3}$ alkyl-O-glucuronidyl;" should read --$R_1$ is H, $C_{1-3}$ alkyl, hydroxy-$C_{1-3}$ alkyl, $C_{1-3}$ alkoxy, or $C_{1-3}$ alkyl-O-glucuronidyl;-- |